(12) United States Patent
Chen et al.

(10) Patent No.: US 7,376,644 B2
(45) Date of Patent: May 20, 2008

(54) KNOWLEDGE PORTAL FOR ACCESSING, ANALYZING AND STANDARDIZING DATA

(75) Inventors: Xiao Chen, Naperville, IL (US);
Erh-An Huang, Westmont, IL (US);
Scott Milkovich, Glen Ellyn, IL (US);
Eugene Rider, Oak Brook, IL (US)

(73) Assignee: RAM Consulting Inc., Oak Brook, IL (US)

( * ) Notice: Subject to any disclaimer, the term of this patent is extended or adjusted under 35 U.S.C. 154(b) by 613 days.

(21) Appl. No.: 10/923,691

(22) Filed: Aug. 24, 2004

(65) Prior Publication Data

US 2005/0171941 A1    Aug. 4, 2005

Related U.S. Application Data

(60) Provisional application No. 60/540,325, filed on Feb. 2, 2004.

(51) Int. Cl.
*G06F 7/00* (2006.01)
*G06F 17/30* (2006.01)

(52) U.S. Cl. .............................. 707/3; 707/4
(58) Field of Classification Search ............ 707/3, 707/4, 10, 1; 705/1, 2, 38; 340/905
See application file for complete search history.

(56) References Cited

U.S. PATENT DOCUMENTS 6,065,000 A * 5/2000 Jensen ........................ 707/3
6,807,569 B1 * 10/2004 Bhimani et al. ............ 709/217
6,989,765 B2 * 1/2006 Gueziec .................... 340/905
2002/0165852 A1 11/2002 Gogolak
2002/0165853 A1 11/2002 Gogolak
2003/0120514 A1 6/2003 Rao et al.
2003/0135378 A1 * 7/2003 Carlson et al. .............. 705/1
2005/0177393 A1 * 8/2005 Sacco et al. ................. 705/2
2005/0198556 A1 * 9/2005 Tripp et al. ................ 714/726

FOREIGN PATENT DOCUMENTS

WO    WO 02/088900    11/2002
WO    WO 03/021389    3/2003

* cited by examiner

*Primary Examiner*—Don Wong
*Assistant Examiner*—Merilyn P Nguyen
(74) *Attorney, Agent, or Firm*—McGuireWoods LLP

(57) ABSTRACT

A method and system is provided to access one or more historical incident databases, for example, CDC, CPSC, DTI, AAPCC and the like, for standardizing the potentially differing categories and coding among the databases. The standardizing includes recoding of the categories by providing a unified set of categories reflective of similar categories found among the one or more databases, if any. Submission of search queries allows users to obtain unified data across the databases so that incident history statistics for one or more products tracked by commonly available databases may be easily acquired. The resulting reports and statistics may be used by various entities to understand historical incidents from multiple perspectives including, for example, injury and fatality statistics as a function of age group, type of injury, time periods, diagnosis, injury outcome, severity, and the like. Data may be presented in standardized formats or in any of the native database formats.

49 Claims, 17 Drawing Sheets

| US NATIONAL ESTIMATES VS. YEAR | | |
|---|---|---|
| YEAR | FREQUENCY | US ESTIMATE |
| 1990 | 24 | 1,551 |
| 1991 | 39 | 1,692 |
| 1992 | 44 | 1,931 |
| 1993 | 46 | 1,881 |
| 1994 | 57 | 2,420 |

| AGE DISTRIBUTION | | | |
|---|---|---|---|
| AGE | FREQUENCY | PERCENT | CUMULATIVE PERCENT |
| 0 | 4 | 1.9% | 1.9% |
| 1 | 22 | 10.6% | 12.6% |
| 2 | 23 | 11.1% | 23.7% |
| 3 | 33 | 15.9% | 39.6% |
| 4 | 21 | 10.1% | 49.8% |
| 5 | 11 | 5.3% | 55.1% |
| 6 | 11 | 5.3% | 60.4% |
| 7 | 8 | 3.9% | 64.3% |
| 8 | 8 | 3.9% | 68.1% |
| 9 | 6 | 2.9% | 71.0% |
| 10 | 4 | 1.9% | 72.9% |
| 11 | 10 | 4.8% | 77.8% |
| 12 | 3 | 1.4% | 79.2% |
| 13 | 5 | 2.4% | 81.6% |
| 15-24 | 16 | 7.7% | 89.4% |
| 25-34 | 15 | 7.2% | 96.6% |
| 35-44 | 5 | 2.4% | 99.0% |
| 45-54 | 1 | 0.5% | 99.5% |
| 55-64 | 1 | 0.5% | 100.0% |
| TOTAL | 207 | 100.0% | 100.0% |

*FIG. 1E*

| DIAGNOSIS | | |
|---|---|---|
| DIAGNOSIS | FREQUENCY | PERCENT |
| CONTUSIONS, ABRASIONS | 98 | 46.7% |
| LACERATION | 47 | 22.4% |
| PUNCTURE | 20 | 9.5% |
| FOREIGN BODY | 13 | 6.2% |
| INGESTED FOREIGN OBJECT | 13 | 6.2% |
| OTHER | 9 | 4.3% |
| HEMORRHAGE | 4 | 1.9% |
| DERMATITIS, CONJUNCTIVITIS | 2 | 1.0% |
| ASPIRATED FOREIGN OBJECT | 1 | 0.5% |
| BURNS, SCALD | 1 | 0.5% |
| DENTAL INJURY | 1 | 0.5% |
| BURNS, THERMAL | 1 | 0.5% |
| TOTAL | 210 | 100.0% |

*FIG. 1H*

| BODY PART | | |
|---|---|---|
| BODY PART | FREQUENCY | PERCENT |
| MOUTH | 80 | 38.1% |
| EYEBALL | 64 | 30.5% |
| EAR | 19 | 9.0% |
| NECK | 16 | 7.6% |
| INTERNAL | 14 | 6.7% |
| FACE | 12 | 5.7% |
| ALL PARTS OF BODY | 1 | 0.5% |
| HAND | 1 | 0.5% |
| TRUNK, LOWER | 1 | 0.5% |
| TRUNK, UPPER | 1 | 0.5% |
| HEAD | 1 | 0.5% |
| TOTAL | 210 | 100.0% |

| DISPOSITION | | |
|---|---|---|
| DISPOSITION | FREQUENCY | PERCENT |
| TREATED AND RELEASED | 208 | 99.0% |
| HOSPITALIZED | 1 | 0.5% |
| TRANSFERRED | 1 | 0.5% |
| TOTAL | 210 | 100.0% |

- 300
- 305 — QUERY SUMMARY | INJURY RECORD | FATALITY REC. | IPII | INDP | TEXT INPUT
- SUBMIT / REPORT
- 345 — QUERY RESULTS
  - YEARS | SAMPLE COUNT | ANNUAL NAT'NL EST. | SAMPLE HOSP. RATE
  - INJURY — %
  - FATALITY — N/A
- 310 — QUERY INPUTS
- 315 — YEARS: FROM [ ] TO [ ]  AGE: FROM [ ] TO [ ]
- PRODUCT CODE
- 325
- DESCRIPTION KEYWORDS
- 350

FIG. 3B

- 300
- QUERY SUMMARY | INJURY RECORD | FATALITY REC. | IPII | INDP | TEXT INPUT
- ram(s)
- FILTER | RUN | BACK TO RECORDS | PREVIOUS [ ] / [ ] NEXT
- RECORDS EXPORT
- YEAR [ ]   AGE [ ]
- DIAGNOSIS [ ]  PROD. CODE [ ]  LOCATION [ ]
- BODY PART
- DISPOSITION
- DESCRIPTION

KNOWLEDGE PORTAL FOR ACCESSING, ANALYZING AND STANDARDIZING DATA

CROSS-REFERENCE TO RELATED APPLICATIONS

This application claims priority to U.S. Provisional Patent Application No. 60/540,325, filed on Feb. 2, 2004 and which is incorporated herein in its entirety by reference.

BACKGROUND OF THE INVENTION

1. Field of the Invention

The invention generally relates to a system and method of accessing one or more incident databases, and more particularly, to a system and method of standardizing data content of one or more incident databases for query and comparative usage.

2. Background Description

Historical product performance and risk assessment is important information for decision making, for example, to identify positive or negative product performance by segments of society, age groups, geographic areas, or the like. If a product is found to have poor performance, a manufacturer may elect not to introduce the item, or perhaps, choose to redesign the product to increase its performance. Alternatively, product performance of a device by a manufacturer may demonstrate the manufacture's care in designing the device, or to show that the manufacturer has considered performance prior to its introduction into the marketplace. These product performances may also be used to educate the consumer, manufacturer, distributor and/or retailer about a product or class of products. This assessment of product performance may also be used to ensure the quality of the products also devised to avoid and/or minimize adverse customer and public relations.

Additionally, historical incident data may be useful for other reasons and used by different types of users such as researchers, professionals, institutions, consumers, or the like, for trend analysis, decision making of various types, or commercial advantage. However, in order to evaluate products, historical data, for example, injury and fatality data must be accessible for products.

Data associated with a wide breadth of products are currently tracked by several entities. For example, the United States Consumer Product Safety Commission using the National Electronic Injury Surveillance System (NEISS). NEISS provides a product coding system (typically a four-digit code) for a wide variety of products ranging from clothing, equipment, and appliances, to toys, etc. Other exemplary databases include American Association of Poison Control Centers (AAPCC), Children's Hospital Choking Database (CHD), Centers for Disease Control and Prevention (CDC), The Department for Trade & Industry (DTI) (UK), The Office for National Statistics (ONS) (UK), and Health Canada (HC). Each of these databases tracks essential historical data that may be used to evaluate products.

However, each of these databases typically implements data formatting and coding in a unique manner. For example, product codes may be different, product characteristics that are tracked may be different, and historical events may be characterized by different aspects. Further, each of these databases typically resides in a different geographic location and is maintained by a different entity. These disparities between these exemplary databases create a user barrier for effectively accessing and interpreting the data contained in the databases. That is, it may very difficult, if not impossible, to analyze the data across these databases in a meaningful way. For example, it is very difficult to effectively obtain a standardized and unified representation of equivalent or pertinent data contained in any combination of these databases due to the varying formats and coding. In fact, one database may contain certain products, while others may not which only exasperates the problem. Thus, providing a standardized coding from different databases, which does not currently exist can provide great benefits to the accumulation and analysis of data across different databases. The invention overcomes one or more of the above problems.

SUMMARY OF THE INVENTION

In an aspect of the invention, a method of searching databases is provided that include accessing one or more databases each having historical incident data classified into categories or fields. The invention then provides for standardizing at least one of the categories of the historical incident data in the one or more databases by correlating incident data to a predetermined format and providing one or more outputs associated with the predetermined format for analysis.

In another aspect of the invention, a method for searching databases is provided. The method comprises accessing historical incident data from a plurality of databases having different coding representing categories, recoding the different coding to provide a standardized coding of the historical incident data and outputting unified historical incident data from the plurality of databases using the standardized coding to create standardized categories.

In another aspect of the invention, a method for standardizing data is provided. The method comprises the steps of recognizing one or more categories in one or more databases, each of the one or more databases having historical incident data. The method includes associating the one or more categories based on one or more related characteristics to a pre-determined category format and querying the historical incident data using the pre-determined category format to obtain statistical information for outputting.

In another aspect of the invention, a computer program product is provided comprising a computer usable medium having readable program code embodied in the medium, the computer program product includes at least one component to access one or more databases each having historical incident data classified into categories, standardize at least one of the categories of the historical incident data in the one or more databases by correlating incident data to a predetermined format and provide one or more outputs associated with the predetermined format for analysis.

BRIEF DESCRIPTION OF THE DRAWINGS

FIGS. 1C-1M are embodiments of reports produced in accordance with the invention;

FIGS. 2A-2E are embodiments of graphical user interfaces, according to the invention;

FIG. 3A-3E are embodiments of graphical user interfaces, according to the invention;

DETAILED DESCRIPTION OF EMBODIMENTS OF THE INVENTION

Figures 1A, 1B:
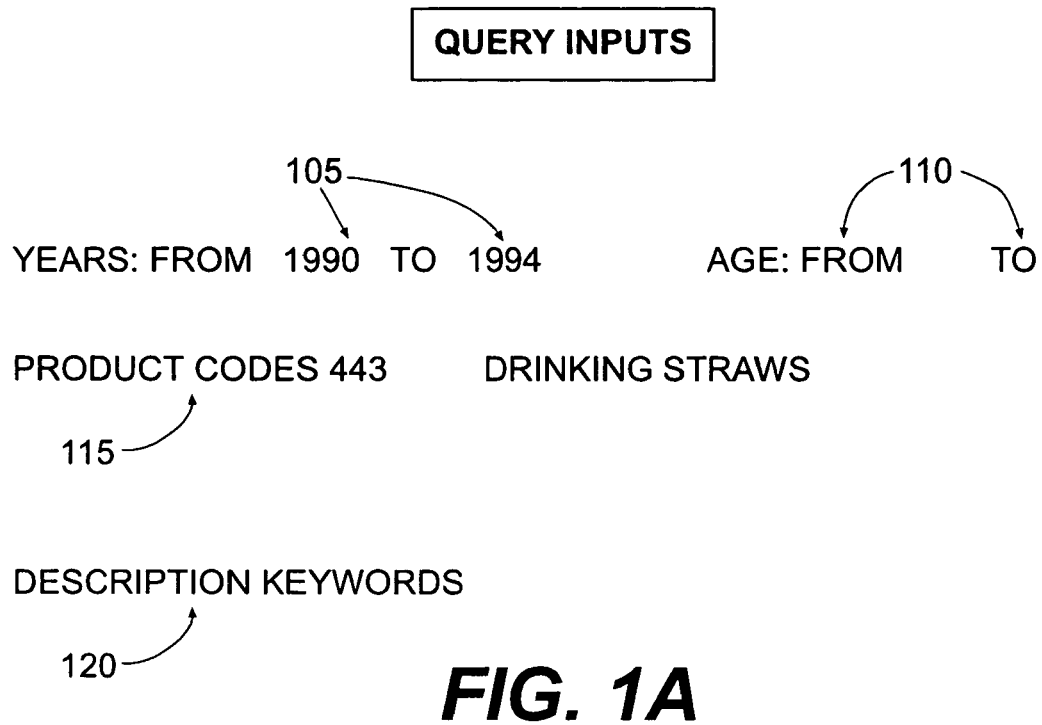
FIG. 1A is an embodiment of a user query input for querying databases.
FIG. 1B is an embodiment of query results summary using the embodiment of FIG. 1A.

The invention relates to a system and method of accessing, mining, and effectively centralizing data from various databases. The databases include, but are not limited to, a plurality of disparate incident, injury, and/or fatality databases typically characterized by different formats, terminologies, focuses, contents, structures, and/or languages and that may currently or traditionally be used by practitioners in widely varying and seemingly unrelated fields of endeavor.

For example, the U.S. Consumer Product Safety Commission (CPSC) databases contain consumer-product-related historical injury and fatality data in fields such as severity and etiology of injury. Other databases such as those of the U.S. Centers for Disease Control and Prevention (CDC), for example, contain data that are significantly different from those of the CPSC databases, traditionally of interest to a different group of practitioners, and that may exist in widely differing formats or field structures. Data from yet other databases, such as the Injury Database (IDB) of the European Union, Canadian Hospital Injury Reporting and Prevention Program (CHIRPP) of Health Canada, and other private or public databases, may be used by practitioners in widely varying fields of endeavor, and contain data in widely differing formats, contents, and structures, and may have been created to achieve unrelated goals.

Table 1 illustrates the nature of representative data that may be included in the various databases by topic. For exemplary purposes, Table 1 shows data that may be found in the representative databases for various categories of products. However, it should be understood that different data and table structures are also contemplated for use in accordance with the invention.

Referring to Table 1, the column "Source/Database" denotes which database(s) is involved and any sub-categories of such databases. For example, the CPSC source may include information relating to accident investigation. "N" is the total number of raw records currently available in the database. "Dates" refers to the years for which data are available in each database. For example, the database for accident investigation (CPSC) may include 763,030 records for dates 1983-2002. Further information may include "Incidents," "Injuries," "Fatalities," and "Comments" which are indicators signifying whether the specific database contains this type of data. For example, the AAPCC database contains 81,946 records associated with various categories of products for the two years 1988-1989 and contains incident information, only.

In the invention, a method and system is contemplated to convert some or all of the data from Table 1 into a standardized set of data. Of course, different data sources and data formats are also contemplated for use by the invention and Table 1 as well as the other Tables and Figures should not be construed as limiting factors of the invention. This allows for accurate information, categorization, and analysis across different databases, sets of data, and what appears to be disparate information. That is, the invention is able to standardize and recode the data from the exemplary sources of Table 1, for instance, into a standardized format for comparison and analysis.

Table 2 is an embodiment of standardizing and recoding of pre-coded data (e.g., category definitions) from different sources into a standardized format to allow for comparison across different data sources, according to the invention. Any number of data sources may be standardized and recoded, as well as any number of categories. Thus, the illustrative example of Table 2, reproduced below, is not a limiting feature of the invention.

TABLE 1

| Source/Database | | N | Dates | Years | INCIDENTS | INJURIES | FATALITIES | COMMENTS |
|---|---|---|---|---|---|---|---|---|
| | AAPCC | 81,946 | 1988-1989 | 2 | X | | | |
| CHD | North America | 5,528 | 1989-1998 | 10 | | X | | X |
| | Europe, S. Pacific, ME | 1,772 | 1994-2000 | 7 | | X | | X |
| | South Africa | 340 | 1996-2000 | 5 | | X | | X |
| | Far East | 136 | 1999-2001 | 3 | | X | | X |
| CPSC | NEISS | 5,050,146 | 1983-2002 | 20 | | X | | X |
| | Reported Incidents | 362,509 | 1983-2002 | 20 | X | X | X | X |
| | Accident Investigation | 763,030 | 1983-2002 | 20 | | X | X | X |
| | Death Certificate Files | 88,420 | 1983-2002 | 20 | | | X | X |
| CDC | NEAIP | 231,672 | 2000 | 0.5 | | X | X | X |
| DTI | LASS, HASS, HADD | 1,280,769 | 1985-1999 | 15 | | X | X | X |
| ONS | | 1,335 | 1998-2001 | 2 | | | X | X |
| HC | CHIRPP | 17,406 | 1990-2001 | 12 | | X | | X |
| | TOTAL | 7,198,282 | | | | | | |

TABLE 2

| Standardized Codes | CPSC (NEISS/IPII/INDP/DTHS) | DTI (HASS/LASS/HADD) |
|---|---|---|
| Treated & Released | Treated and released, or examined and released | Treated; no more treatment required; Referred to any outpatient clinic Referred to GP Examined but no treatment given |
| Transferred | Treated and transferred to another hospital | Referred to other hospital |
| Hospitalized | Treated and transferred for hospitalization | Discharged IP, referred outpatient clinic Discharged IP, referred to GP Discharged IP, referred OP/GP (unsp which) |
| | Treated and admitted for hospitalization within the same facility | Discharged IP, no more treatment required Admitted to specialist hospital Admitted to other hospital IP for less than one day |
| Death | DOA or died in emergency department | DOA or death or died after admission as inpatient |
| Unknown | Not recorded | Patient did not wait Unknown outcome |

In the example of Table 2, three columns are shown which represent the new standardized codes for the CPSC and DTI databases. Specifically, the invention is capable of recoding the database information by looking for common keywords or phrase, for example, throughout the entire realm of applicable databases. Once the keywords or phrases are found, a confidence analysis can be performed to determine the strength of the associations between these keywords and/or phrases. Thereafter, or in conjunction with the looking step, the invention may then use the information (e.g., database information) associated with the keyword and/or phrase for recoding or making new associations to standardized codes.

For example, the invention may recode all of the common keywords or phrases with a new designation (e.g., word and/or number). In one embodiment, look-up tables may be built to make such associations. In this way, standardization can be accomplished, in one embodiment. These steps may be performed (i) prior to any request by a user (e.g., as an off-line function which creates standardized data for subsequent searching) or (ii) in real time when a user is actually entering in the keywords and parameters, as shown for example, by data entry of FIGS. 1A-2E. A manual categorization or recoding of the information of one or more databases to standardize the information contained therein is also contemplated. Table 2 shows this process, in table format.

In Table 2, column 1 represents "Standardized Codes" generated by the invention that corresponds to the codes from the CPSC database (and databases similar to CPSC) represented in Column 2 (and the DTI database represented in Column 3), such as for example, "Treated and released" or "examined and released" which are recoded by the invention as "Treated and Released." Further, categories from the DTI database (and database similar to DTI) shown in Column 3, such as for example, "Treated; no more treatment required", "Referred to any outpatient clinic", "Referred to GP" and "Examined but no treatment given", categories are also recoded by the invention as "Treated and Released". This recoding establishes an equivalence among related categories of Column 2 and Column 3.

Likewise, "Treated and transferred to another hospital" (CPSC database) and "Referred to other hospital" (DTI) may be recoded to "Transferred" by the invention. Further, "Treated and transferred for hospitalization" and "treated and admitted for hospitalization within the same facility" (CPCS database) and seven codes from the DTI database, namely, (i) "Discharged IP, referred outpatient clinic",
(ii) "Discharged IP, referred to GP",
(iii) "Discharged IP, referred OP/GP (unsp which)",
(iv) "Discharged IP, no more treatment required",
(v) "Admitted to specialist hospital",
(vi) "Admitted to other hospital", and
(vii) "IP for less than one day"

are recoded by the invention to the standardized code "Hospitalized." The recoding is similarly generated for "Death" and "Unknown". Any coding method from any number of sources may be recoded and standardized by the invention, with the example of Table 2 being but one example.

Table 3 is an embodiment of standardization and recoding of definitions and representative code assignments from a plurality of database sources.

TABLE 3

| STANDARDIZED | | CPSC (NEISS/IPII/INDP/DTHS) | | HEALTH CANADA(CHIRPP) | |
|---|---|---|---|---|---|
| Code | Definition | Code | Definition | Code | Definition |
| 101 | Treated & Released | 1 | Treated and released, or examined and released | 2 | Advice Only |
| | | | | 3 | Treated, follow-up PRN |
| | | | | 4 | Treated, follow-up required |

TABLE 3-continued

| STANDARDIZED | | CPSC (NEISS/IPII/INDP/DTHS) | | HEALTH CANADA(CHIRPP) | |
|---|---|---|---|---|---|
| Code | Definition | Code | Definition | Code | Definition |
| | | | | 7 | Short stay, observation in emergency |
| 102 | Transferred | 2 | Treated and transferred to another hospital | 7 | Transferred to another hospital |
| 103 | Hospitalized | 3 | Treated and transferred for hospitalization | 6 | Admitted to this hospital |
| | | 4 | Treated and admitted for hospitalization within the same facility | | |
| 104 | Death | 8 | DOA or died in emergency department | 8 | Dead on arrival or died in emergency |
| 105 | Unknown | 9 | Not recorded | 1 | Left without being seen |

Referring to Table 3, source databases, CPSC and similarly formatted databases (e.g., NEISS, IPII, INDP, DTHS) and Health Canada (different formatting from CPSC) and their respective coding and coding definitions are shown. Standardized re-coding, as provided by the invention, is shown under the title STANDARDIZED and includes the recoded codes, under the sub-title Code (e.g., 101-105) and corresponding category definitions, under sub-title Definition (e.g., "Treated & Released," "Transferred," "Hospitalized," "Death," and "Unknown"). This recoding provision of the invention provides a normalization of disparate coding and definitions from different database sources to provide standardized categories.

For example, the standardized code "103" has a corresponding definition of "Hospitalized" and is the result of a recoding of two CPSC codes "3" and "4" which have the definitions of "Treated and transferred for hospitalization" and "Treated and admitted for hospitalization within the same facility," respectively. Further, the standardized code "103" is also the result of identification of an equivalent code from the Health Canada database (and database similar to CHIRPP database). In this example, the Health Canada code "6" and associated definition "Admitted to this hospital" is recoded to a standardized code of "103" with definition "Hospitalized."

The embodiment of Table 3 also shows that a set of codes from source databases (e.g., Health Canada codes "2-5") may be collectively recoded to a single standardized code (e.g., "101") along with the corresponding multiple definitions collectively unified to a single standardized definition (e.g., "Treated and Released"). The codes may be a partial recoding of one of the source databases or a full recoding. In embodiments, the recoding of the invention may use the pre-existing coding from one of the source databases as the standardized coding, either in whole or in part, which maintains, to some degree, familiarity for certain users already knowledgeable with a particular coding technique.

The standardized recoding provided by the invention, as illustrated in the embodiments of Tables 2 and 3, allows for access of data across a plurality of databases with differing field structures and formats. The invention applies predefined uniform field structures, formats, and coding categories so that common standardized categories and ratings may be available for consumers, manufacturers, professional use, and the like. The invention also provides a user the option of viewing data from a single database in its original format or simultaneously viewing and comparing data from a plurality of databases. In the latter case the invention converts the data, as necessary, to a standard format and provides the ability to view the data re-presented in any or all representative formats native to the queried databases, or in standard formats generated by the invention.

By way of illustrative example, and referring to FIGS. 1A and 1B, the invention provides the ability for users to query on data across selected or multiple databases by various parameters (e.g., age, product, year, and/or description key words), and also creates a formatted output of the queries by desired query parameters. FIG. 1A is an embodiment of a user query input for querying databases. Data may already be recoded for searching or searching may be performed in real-time with recoding occurring in real-time. The query input includes input fields for specifying, for example, a range of years 105, range of age 110, product codes 115, and description keywords 120 for engaging one or more searches.

As shown in the example of FIG. 1A, a user may select a year range from 1990 to 1994 with a product code of "443" (denoting drinking straw). The remaining fields may be left blank or populated, depending on the particular search. Of course, the year range or product code may also be left blank, depending on the search.

Figure 4:
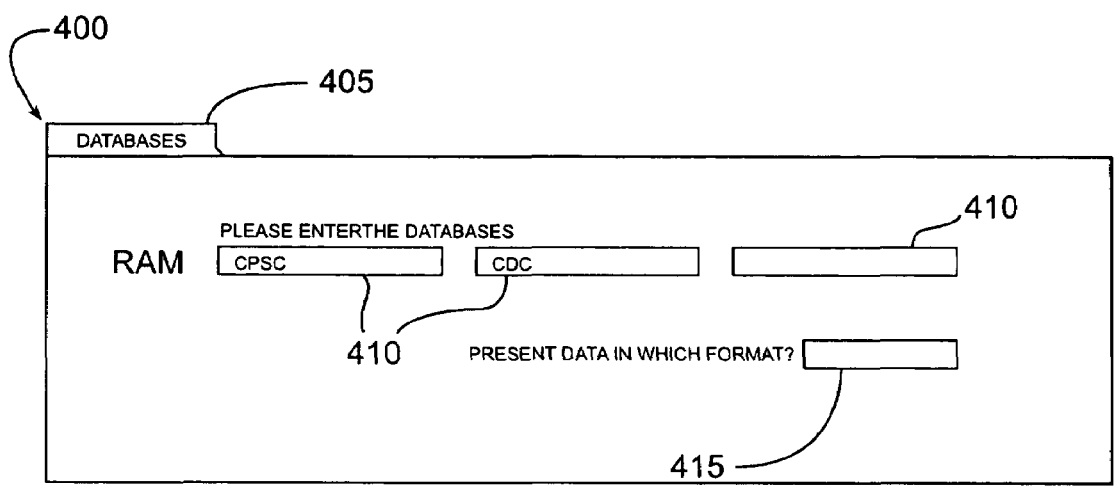
FIG. 4 is an embodiment of a graphical user interface, according to the invention.

As shown in relation to FIG. 4, the user may select one or more databases as the targeted source databases. The invention subsequently accesses the selected database(s) to obtain historical data using the interface methodology native to each accessed database. The search parameters are appropriately applied to each targeted source database reflecting the parameters specified by the exemplary query inputs of FIG. 1A.

FIG. 1B is an embodiment illustrating query results (standardized) using query inputs (e.g., FIG. 1A), which in this example, shows two categories Injury 125 and Fatality 130 found in the source database(s). The query results shown are for 5 years (1990-1994) and show that a "Sample Count" of "210" in the database for Injury 125, under the heading "Sample Count." The "Sample Count" represents the number of records in the database for the Injury 125 category for the selected years 105. The column entitled "Annual National Est." is an estimate of the average number of records per year for the selected years (e.g., 105). The column entitled "Sample Hosp. Rate" is an indication of the percent of injuries, represented by the "Sample Count" (i.e., "210"), that were hospitalized, in this example, "0.48%." The results also show that no fatalities were found in the records of the source databases(s) over the targeted years, as indicated by the Fatality 130 row.

Figures 1C, 1D:
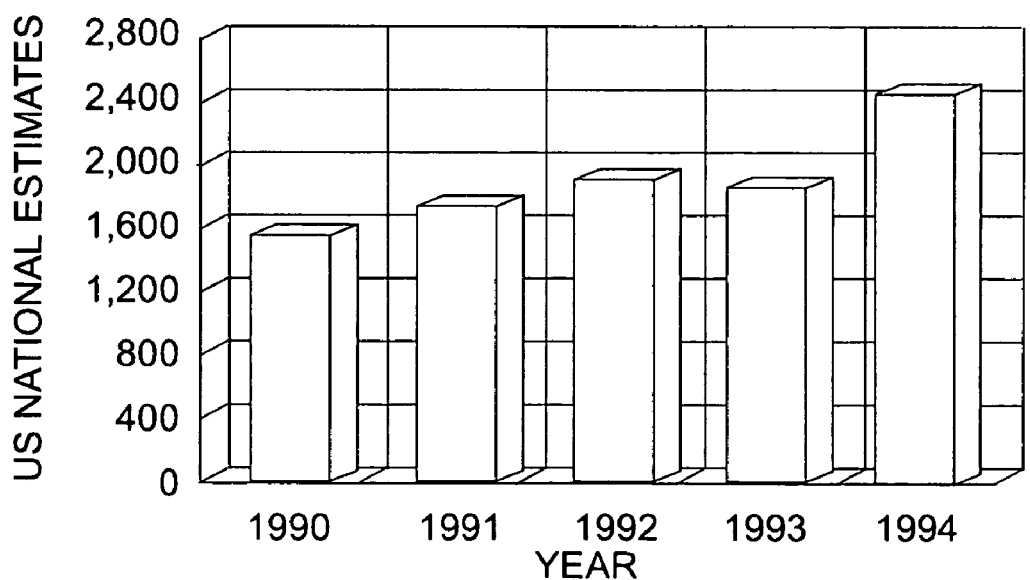

FIG. 1C shows an embodiment of a report provided by a query such as, for example, the query of FIG. 1A. The embodiment of FIG. 1C reflects detailed information, as summarized by FIG. 1B, and includes three columns, the first column, entitled "Year," for each year in the report, the second column, entitled, "Frequency," for showing the actual number of records retrieved by year, and the third column, entitled "U.S. Estimate," for showing the nation-wide estimate number of incidents involving straws by year. For example, in the year 1990, "24" actual records were identified related to "drinking straws" which indicates "1,551" estimated number of nation-wide incidents under "U.S. Estimate." In like manner, the years 1991 through 1994 provide similar information.

FIGS. 1D-1M show several report segments which may be generated by the invention. It should be recognized that other reports may also be generated by the invention, and the reports shown in FIGS. 1D-1M are provided for illustrative purposes. For example, FIG. 1D shows an embodiment of a report produced by the invention in bar-chart format. The data presented represents the "U.S. Estimate" of FIG. 1C and shows the "U.S. Estimate" number of incidents, per year, from 1990 through 1994.

FIG. 1E shows an age distribution report produced by the invention. The age distribution report, for the example of "drinking straw," includes columns "Age", "Frequency", "Percent", and "Cumulative Percent." "Age" shows representative age brackets, "Frequency" shows the actual number of incidents by "Age," "Percent" shows the percent of total incidents by "Age" and "Cumulative Percent" shows a cumulative percentage of incidents by "Age."

Figure 1F:
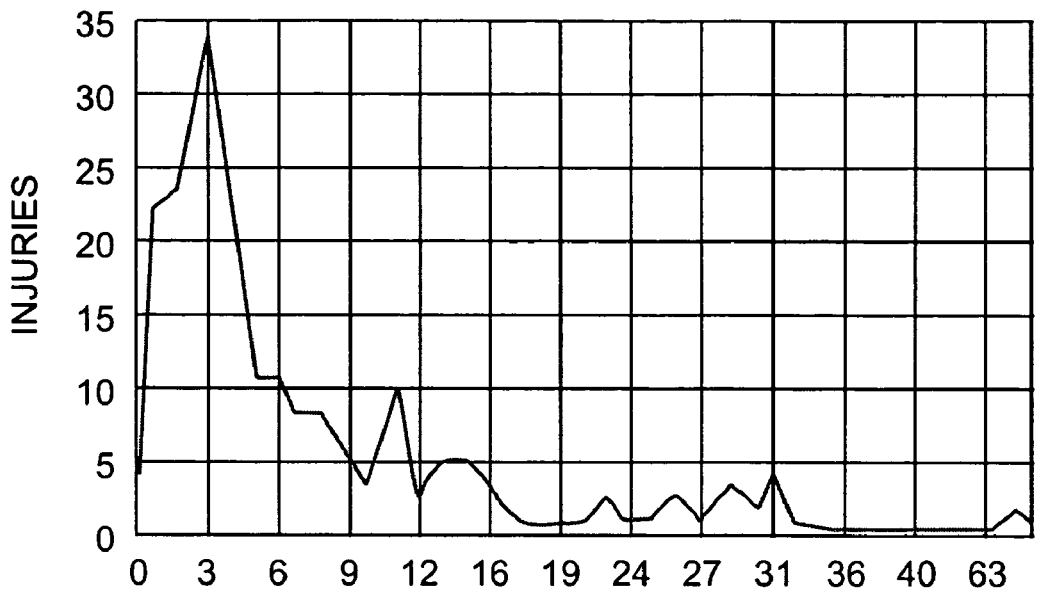
Figure 1G:
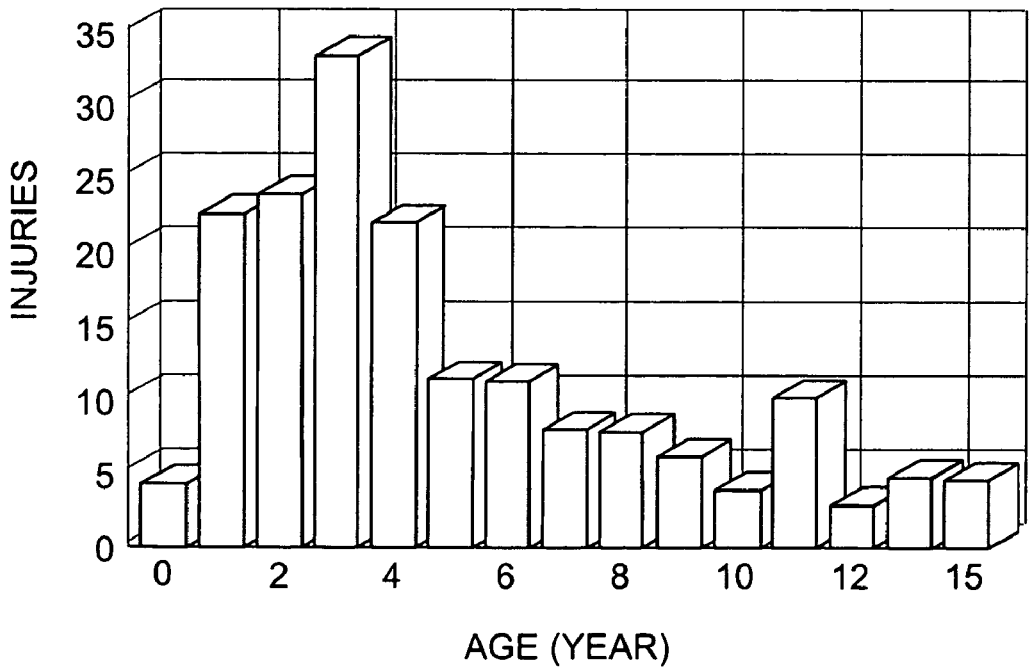

FIG. 1F shows an embodiment of a report produced by the invention that presents, in graph form, the distribution of the frequency of injuries of FIG. 1E by all ages. FIG. 1G shows an embodiment of a report produced by the invention that presents in bar chart form (and may also be a histogram) injuries by age group under fifteen years. These types of reports (e.g., FIGS. 1F and 1G) are useful for ease in recognizing trends and anomalies in data.

Figure 1I:
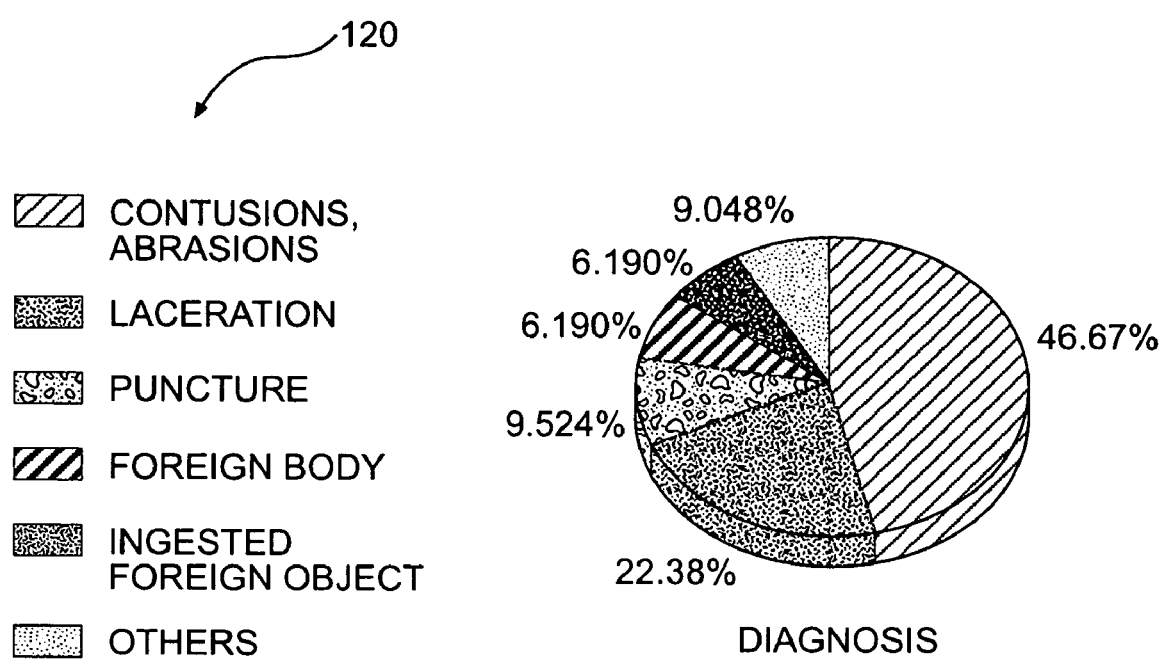

FIG. 1H shows an embodiment of a report produced by the invention that presents a diagnosis breakdown for the injuries caused by "Drinking Straws" as summarized in FIG. 1B. FIG. 1H includes three columns entitled "Diagnosis" which details types of injuries involved, "Frequency" which details the number of actual cases by "Diagnosis", and "Percent" which provides a detailed breakdown of the percentage of each "Diagnosis." For example, "Contusions, Abrasions" comprise "98" incidents of overall injuries for the range of years (e.g., 105 of FIG. 1A) and was "46.7%" of total injuries. In embodiments, other categories (e.g., diagnosis categories) may be included in the embodiment of FIG. 1H as input data necessitates. FIG. 1I is an embodiment of a report showing the breakdown of information of FIG. 1H in pie-chart format with accompanying color-coded key 120.

Figures 1J, 1K:
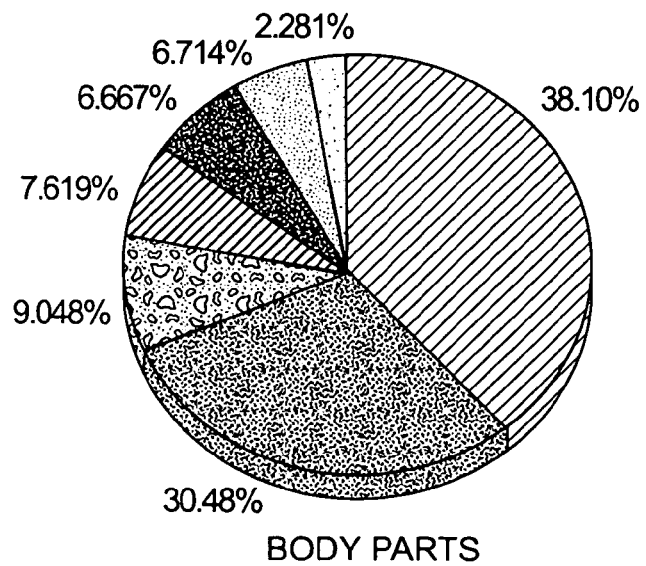

FIG. 1J is an embodiment of a report generated by the invention and includes columns entitled "Body Part," "Frequency," and "Percent." "Body Part" details the body parts involved in the overall injuries of FIGS. 1H and 1J. Also, the columns "Frequency" details the actual injuries to each "Body Part," and "Percent" provides the percentage by "Body Part" of the total number of injuries for the range of years 105. FIG. 1K is an embodiment of a report generated by the invention in pie-chart format for the data of FIG. 1J and includes associated color-coded key 125.

Figures 1L, 1M:
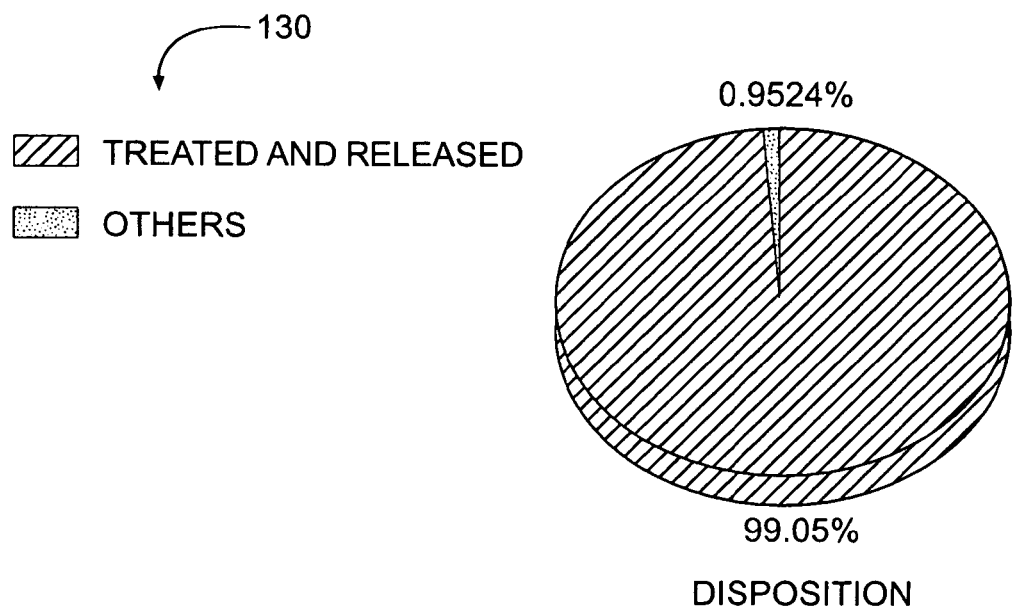

FIG. 1L is an embodiment of a report generated by the invention for disposition of injuries and includes three columns entitled "Disposition," "Frequency," and "Percent." "Disposition" categorizes the results or actions associated with Injury 125 (FIG. 1B). The "210" injuries of FIG. 1B are broken down into categories under the column "Frequency" and by "Percent." The sub-categories of "Disposition" include "Treated and Released," which indicates the number of incidents that resulted in a treatment and release, "Hospitalized," which indicates the number of incidents that resulted in hospitalization, and "Transferred", which indicates the number of incidents that were transferred to other treatment facilities or the like. FIG. 1M is an embodiment of a report in pie-chart format for Disposition (e.g., data of FIG. 1L) and includes a color-coded key 130.

Figures 2A, 2B:
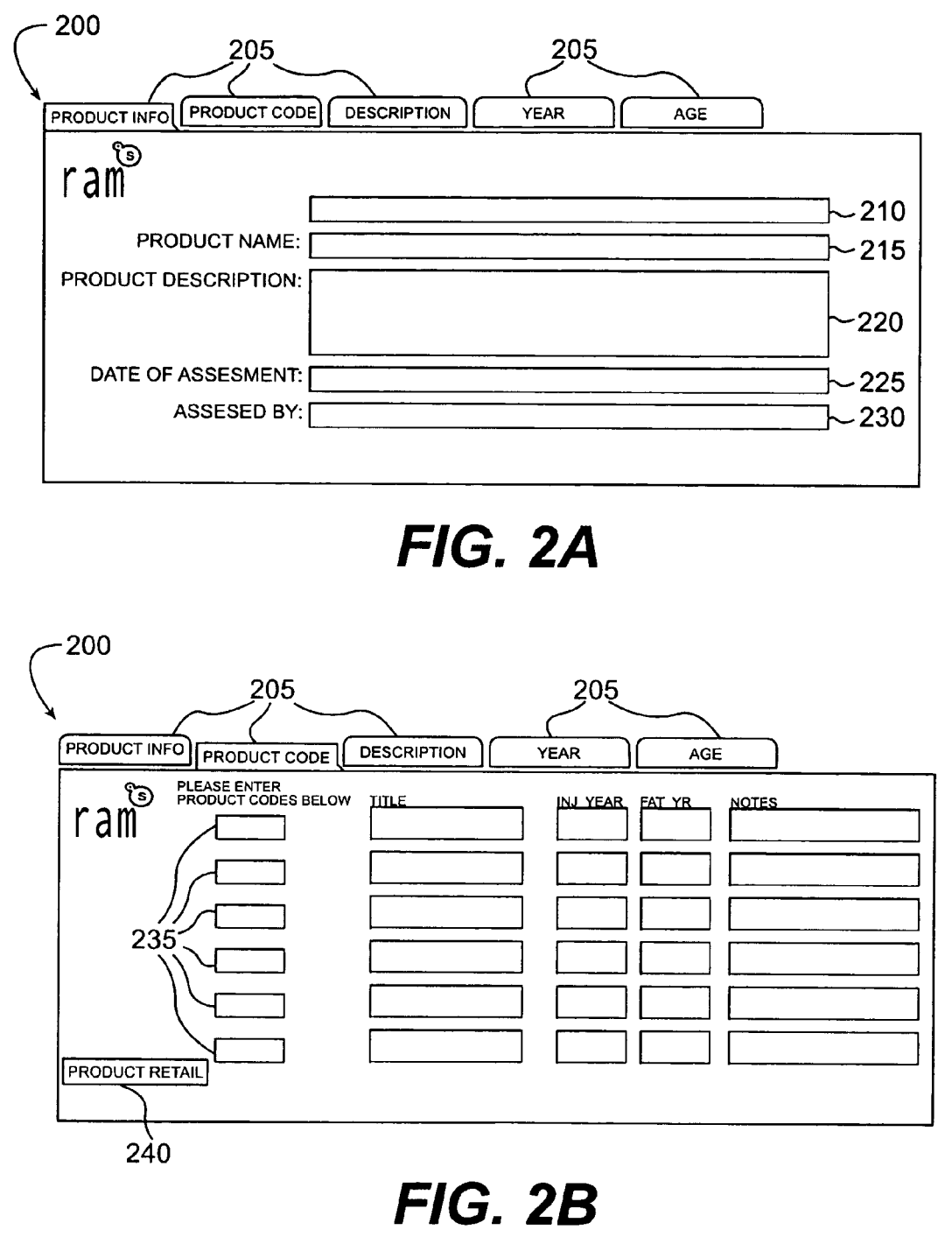
Figure 2C:
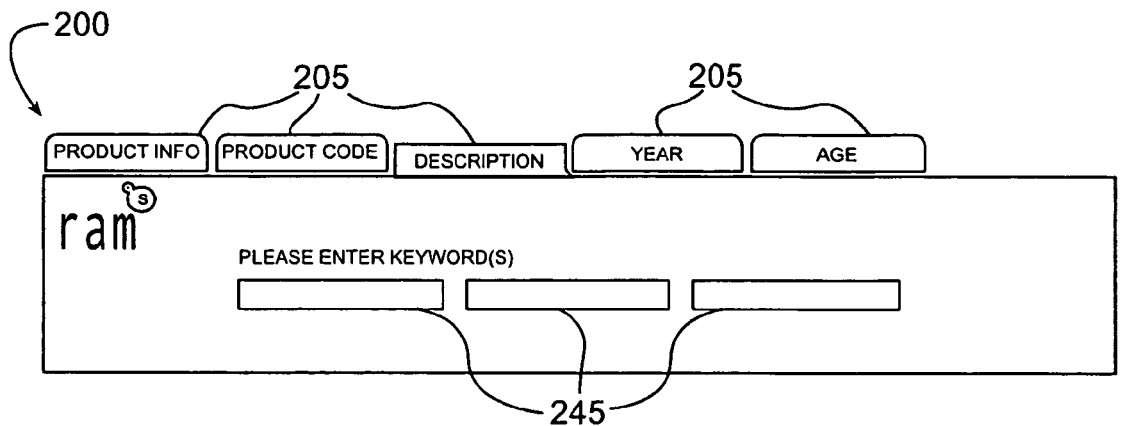
Figure 2D:
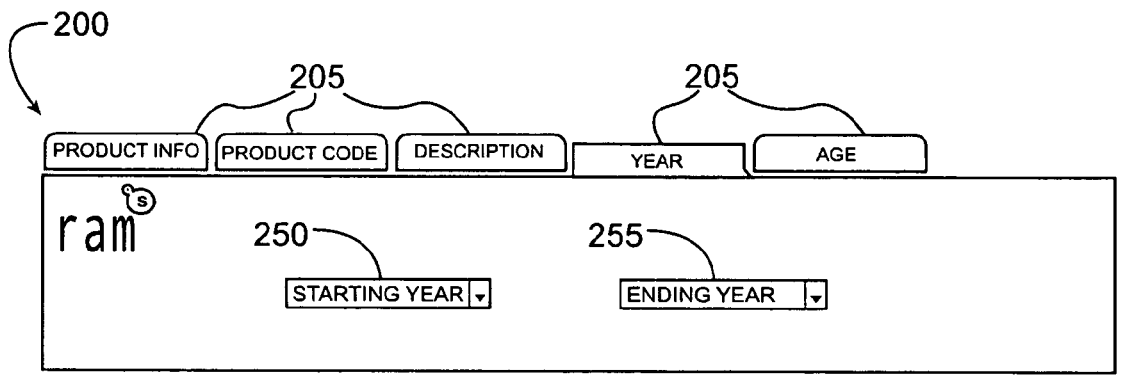

FIGS. 2A-2E are embodiments of graphical user interfaces (GUI), generally denoted by reference numeral 200. The tabs and designations of FIGS. 2A-2E described, herein, are for illustrative purposes and are not limiting features of the invention. For example, the description "Product Info" may be "Product Information," or the like, and such new designations will not have an affect on the underlying functionality of the invention. FIG. 2A is a GUI for establishing an assessment session (e.g., a new or separate use of the invention for accessing historical incident data) and supplying identification information of the assessment session. The navigation tabs 205 provide easy navigation among several GUI screens for receiving various user inputs. Selection of the "Product Info" tab of GUI 200, permits access to input prompts such as a "Project Name" 210 for assigning a name to a project involving the query and assessment session, any "Product name" 215 and "Product Description" 220. Prompts may be provided for recording a "Date of Assessment" 225, and an "Assessed By" 230 (for recording who is performing the assessment).

FIG. 4 is an embodiment of a graphical user interface, denoted generally as reference numeral 400. The GUI 400 may be accessed via a Databases navigation tab 405 (which may also be present, in embodiments, in any GUI of FIGS. 1C-2E). The GUI 400 permits selection of the source databases in the one or more database prompt fields 410. A user may enter the database acronym (e.g., CPSC, CDC, or the like), database code, or other identifier, to select among candidate databases. A database acronym or code may also designate a pre-defined set of databases in order to select multiple databases with one acronym. A prompt 415 may also be provided to select the desired format for displaying reports, e.g., standardized coding or any of the source database formats. If a user selects standardized coding (e.g., STD), then codes provided by the invention that represents the recoded definitions and categories of the source database(s) is used in reports and graphical displays. However, a user may alternatively select any of the native formats of any source database for displaying reports and data (e.g., CPSC, CDC, DTI, or the like).

In use, selecting the Product Code tab of the navigation tabs 205 navigates to the GUI of FIG. 2B which prompts a user for entry of product codes, denoted by reference numeral 235. By entering one or more product codes, a user establishes and identifies the products to be involved in a subsequent query. A Product Detail button 240 may be accessed by a user to review specifications and product information as necessary. A description of the fields in FIG. 2B is provided in Table 4 for illustration purposes as an example of the CPSC database.

TABLE 4

| Column # | COLUMN HEADING | DESCRIPTION |
|---|---|---|
| 1 | Product Code | A four-digit number as in the US CPSC databases |
| 2 | Title | Description of the product (category) corresponding to the product code. |
| 3 | Inj_YR | Time period that the product code is valid for the injury data (in the case of CPSC data, it's NEISS). |
| 4 | Fat_YR | Time period that the product code is valid for the fatality data (in the case of CPSC data, it's IPII/INDP/DTHS). |
| 5 | Notes | Description for changes occurred to the codes. For example, any deletion, combination, split. |

Figure 2E:
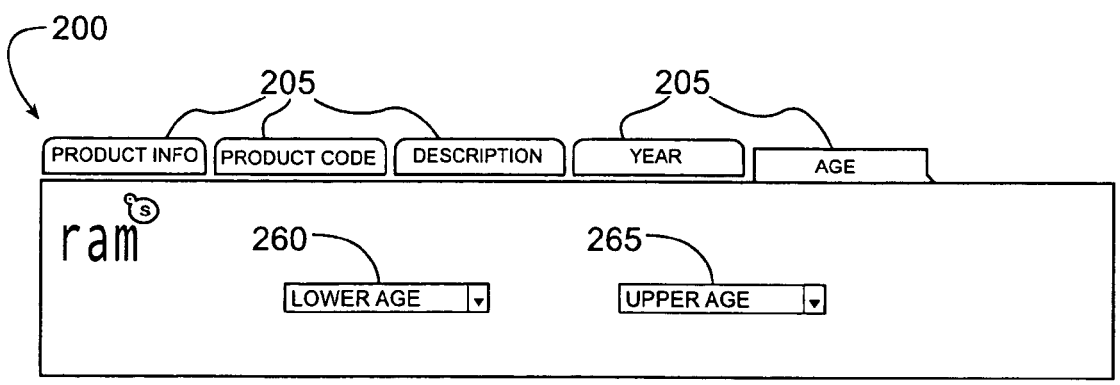

Similarly, selecting the Description tab of navigation tabs 205 navigates to a GUI, depicted by FIG. 2C, which prompts a user to optionally enter one or more keywords 245 in order to refine a product search or, alternatively, to determine a set of products that may be associated with the one or more keywords. Selection of the Year tab of the navigation tabs 205 navigates to a GUI, depicted by FIG. 2D, which prompts for a range of years to define the scope of the subsequent queries and searches. A lower age 260 and an upper age 265 may be entered as necessary by a user, as depicted by FIG. 2E.

FIGS. 3A-3F are embodiments of graphical user interfaces, generally denoted by reference numeral 300. The GUI 300 provides navigation tabs 305 for navigating among several GUI screens associated with querying one or more databases. In embodiments, these navigation tabs 305 may also be present in the GUIs of FIGS. 2A-2E.

In uses, selecting the "Query Summary" tab of navigation tabs 305, presents the GUI options of FIGS. 3A-3E. Any data previously entered via GUIs of FIG. 2A-2E may be presented in appropriate fields shown under Query Inputs 310. For example, the YEARS fields 315 may be initialized with the previously entered range of years. Similarly, the AGE range 320, Product Code 325 (which may be standardized product codes or product codes from any of the target databases), and Description Keywords 330 may also be initialized, as appropriate. Alternatively, a user may edit these fields or initialize any data via the GUIs of FIGS. 2A-2E, for altering limits or ranges, etc.

When a user is satisfied with the parameters of the Query Inputs 310, a query submission may be initiated by selecting the Submit button 340. After a search is completed of the pre-selected databases, a summary of the results is presented. An illustrative display of such a summary is shown under Query Results 345. This summary display is the same as the display as previously discussed in regards to FIG. 1B, and in this example, includes an Injury summary and Fatality summary with a Years indicator (shown as "Years") showing the number of years involved in the summary, a Sample Count indicator (shown as "Sample Count") showing the number of records involved in the summary, Annual National Estimate indicator (shown as "Annual National Est.") showing the estimated annual average and Sample Hospitalization Rate (shown as "Sample Hosp. Rate") showing a percentage of incidents involving hospitalization.

The user may alter any query input field (e.g., and re-submit the query via the GUIs of FIGS. 2A-2E) and may proceed with generation of reports by selecting the Report button 350. Selection of the Report button 340 generates one or more of the reports as previously discussed in relation to FIGS. 1C through 1M. The reports may be presented on a display, written to a file for inclusion in an overall report, printed, or the like. In embodiments, prompts may be presented for selecting which reports are to be generated.

FIG. 3B is a GUI for navigation tab "Injury Record". This navigation tab presents records of injury data (in this case, from NEISS) in forms. Information such as the year that the injury occurred (Year), the age of the victim (Age), the injury diagnosis (Diagnosis), the Product Code, the place where the injury occurred (Location), the injured body part (Body part), the treatment rendered to the victim (Disposition), and a brief narrative of the injury (Description) is provided.

Figures 3C, 3D:
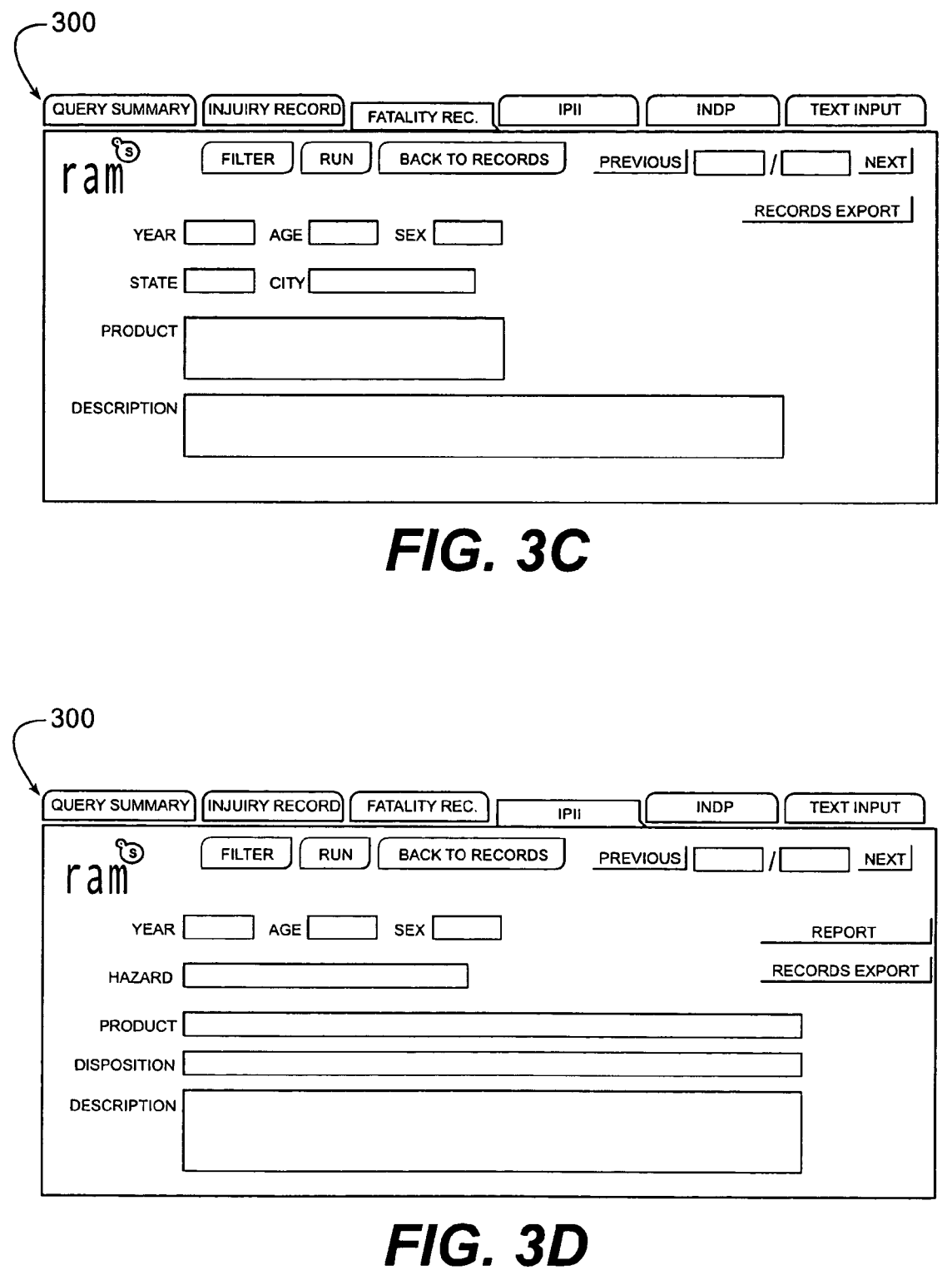

FIG. 3C is a GUI for navigation tab "Fatality Record" and presents records of fatality data (in this case, from IPII/INDP/DTHS) in forms. Information such as the year that the injury occurred (Year), the age and gender (Sex) of the victim, the geographic location where the injury occurred (City and State), the product involved (Product), and the description of the incident (Description) is provided. FIG. 3D is a GUI for navigation tab "IPII" and presents records of the US CPSC Injury/Potential Injury Incident File (IPII) data in forms. Information such as the year that the injury occurred (Year), the age and gender (sex) of the victim, the product involved (Product), the hazard associated with the product (Hazard), the treatment rendered to the victim (Disposition), and a description of the incident (Description) is provided.

Figure 3E:
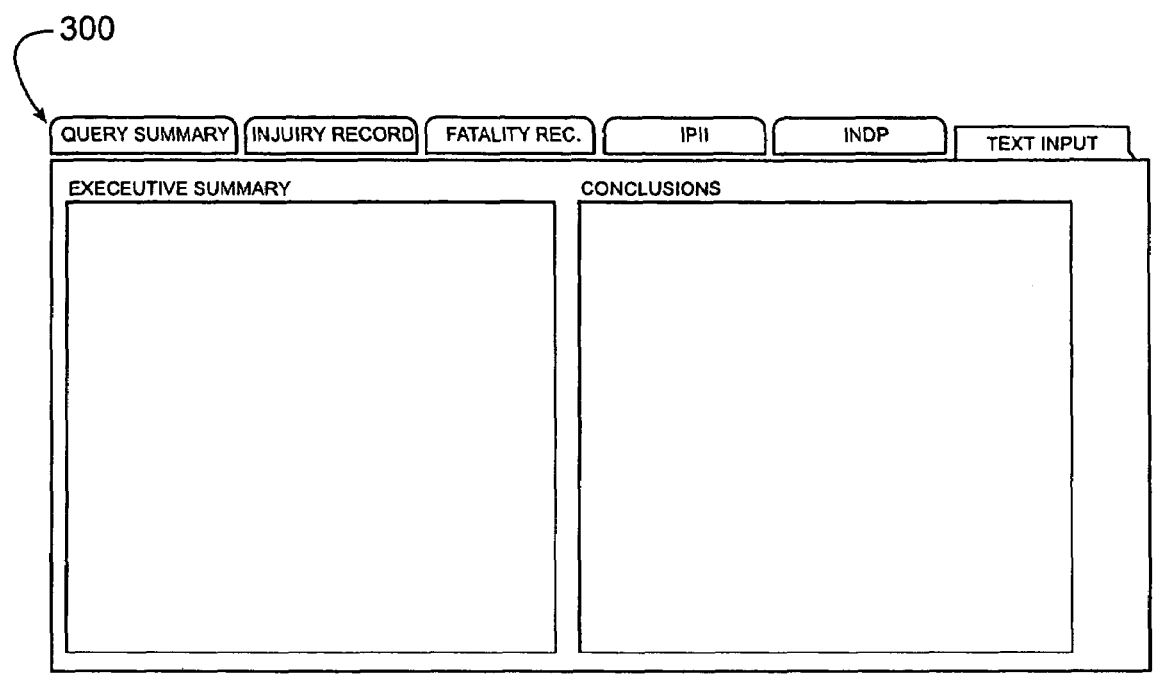

FIG. 3E is a GUI for navigation tab "INDP" and presents records of the US CPSC In-Depth Investigations file in forms. The fields presented for the INDP are typically the same as for the NEISS records (see Injury Record Tab).

FIG. 3F is a GUI for navigation tab "Text Input" and provides the opportunity for the user to enter an Executive Summary and/or Conclusions based on the result records shown under the aforementioned Navigation Tabs highlighted in FIGS. 3A-3E. The Executive Summary and/or Conclusion text give the user the option to summarize, interpret, and/or comment on the analysis results conducted by the invention. For results tab illustrated in FIGS. 3B-3F, the user may review the records in a sequential order by clicking the Previous or Next button. In addition, the user may subjectively include and/or exclude specific records by utilizing the "Filter" function when reviewing records. The final analysis is typically based upon the data set specified by both the query parameters and the customized filtering process, and the finalized data records may be exported to a .pdf file (or the like) for reference.

Figure 5:
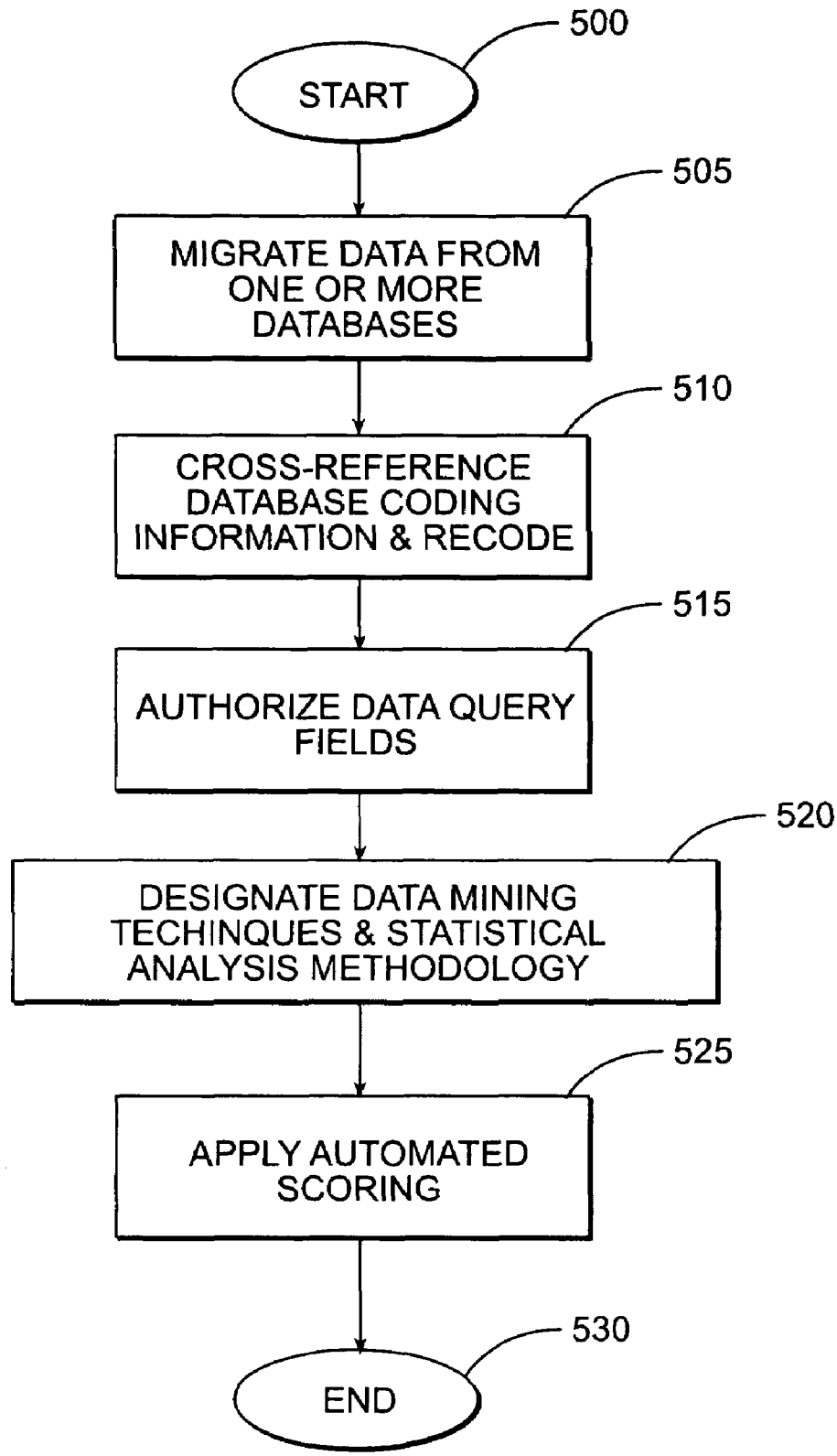
FIG. 5 is a flow diagram of an embodiment showing steps of implementing the invention.

FIG. 5 is a flow diagram of an embodiment of the invention showing steps of constructing/developing the invention, beginning at step 500. FIGS. 5 (and 6-8) may equally represent high-level block diagrams of components of the invention implementing the steps thereof. The steps of FIGS. 5-8 may be implemented on computer program code in combination with the appropriate hardware. This computer program code may be stored on storage media such as a diskette, hard disk, CD-ROM, DVD-ROM or tape, as well as a memory storage device or collection of memory storage devices such as, for example, read-only memory (ROM) or random access memory (RAM). Additionally, the computer program code can be transferred to a workstation over the Internet or some other type of network.

Continuing with FIG. 5, at step 505, data from one of more source databases, that may have dissimilar native formats, is accessed (i.e., read) and migrated to a uniform and harmonized data format that standardizes the information content. The migration translates the data into a common database methodology (such as, for example, Oracle®, Oracle is a registered trademark of Oracle Corporation). At step 510, the data from the one or more databases is cross-referenced and recoded, as necessary, so that the numerical and textual categories are related by commonality (e.g., as discussed previously, this process may include correlating phrases, keywords, topics, manual identification, or the like). Rating systems that may indicate such factors as, for example, severity levels and risk levels as may be used by each database are recognized and translated to a common equivalent rating that provides a standardization of the formats and data. Additionally, a reverse index is maintained so that one database may be expressed in terms of another, or the actual coding and rating of any source database may be available for reference.

At step 515, data query fields are identified and designated so that parameters associated with field formats and data types may be established for accepting search queries. For example, year fields for accepting year range parameters, age fields for accepting age range parameters, product code fields for accepting product codes, or keyword fields for searching for aspects of products and product histories, or the like, are identified and designated for user accessibility. These designations are related to the available data formats, rating systems, and content of the potential source databases and provide a standardized terminology and GUI interfaces for queries.

At step 520, data mining techniques are designated and statistical analysis methodologies are selected for use appropriate to the types of data and formats being searched. Typically, these are generally known data mining and statistical analysis methodologies as one of ordinary skill in the art would recognize which may be selected as appropriate based on actual databases and data content involved.

At step 525, the invention applies automated scoring to the data accessed from the source databases for generating severity codes (such as hazard severity codes) and at-risk scores associated with demographics (e.g., age, population, social attributes, behavior, and the like) by product or product characteristic (e.g., hardness, sharpness, electrical aspect, poisonous aspect, and the like). The invention generates the hospitalization rate for each of the product (category) corresponding to each product code which may vary by data source. The hospitalization rate will be used as an indicator for severity level. Based on that, a visual map (zone chart) is developed to have different zones, in forms of ranges of hospitalization rates, to signify for various severities. In this way, whenever a query is submitted, the hospitalization rate generated from that specific query will be compared to the zone chart. As to the ways of presenting the comparison results, several options are available, including ranking, percentages, and/or color coded qualitative ways such as high, medium, low.

Figure 6:
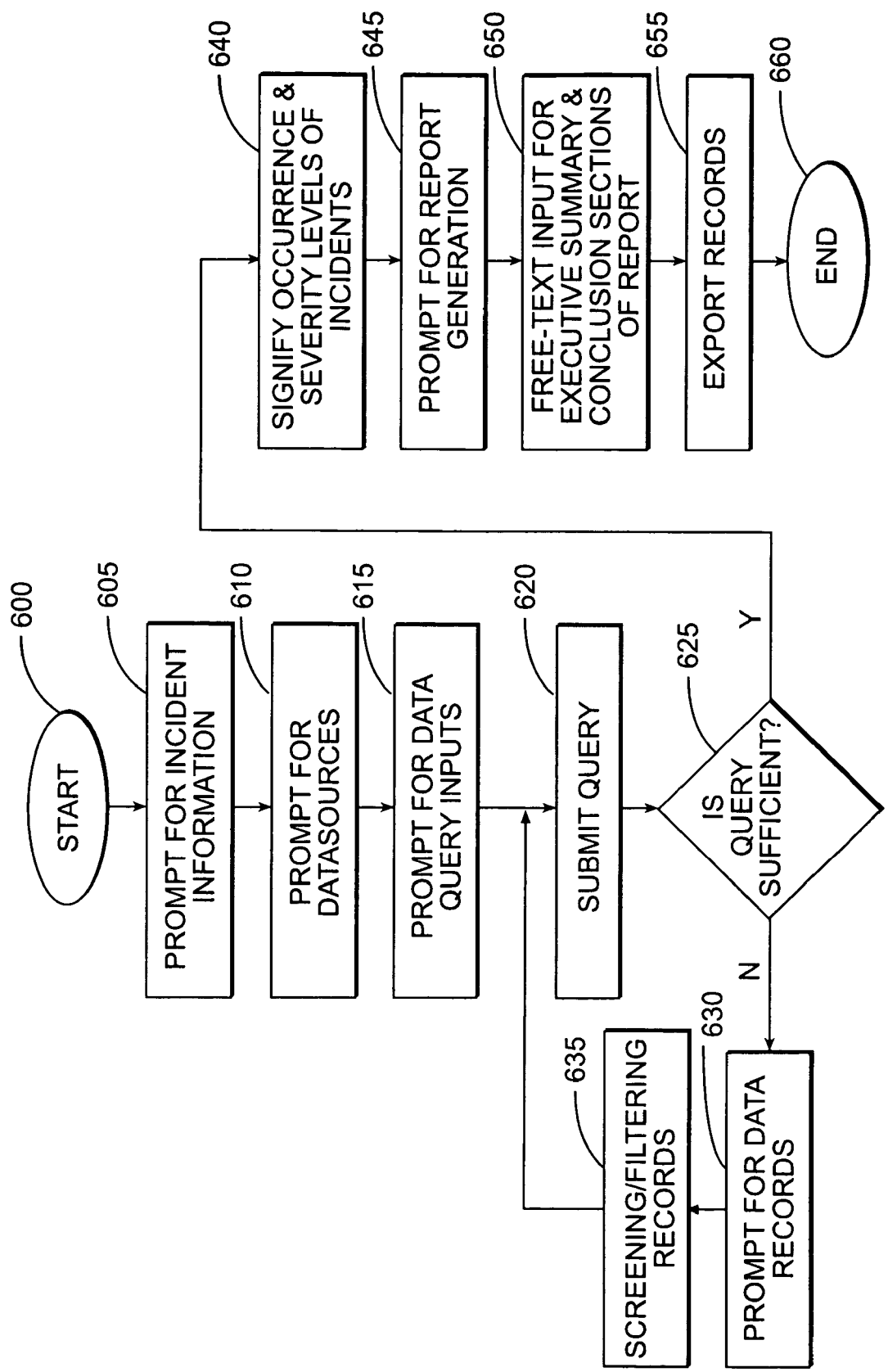
FIG. 6 is a flow chart of an embodiment showing steps of implementing the invention.

FIG. 6 is a flow chart of an embodiment showing steps of using the invention, beginning at step 600. The steps of FIG. 6 may be performed on data that has already been previously accessed and standardized or may be performed on data sources that are accessed in real time and are standardized during the query. At step 605, prompts for product information are provided. The prompts enable input of incident data such as, project name, product name, product description, site of assessment. At step 610, prompts for data sources are provided and permit entry of desired source databases (e.g., CDC, DTI, CPSC, etc.) and, optionally, the desired format (e.g., standardized or any source database format) to be used when presenting subsequent data and reports.

At step 620, a query is submitted which accesses data in the one or more formats from the one or more source databases. When the results of the query are presented to the user, a decision is made whether the query is sufficient, and if not, at step 630, prompts are provided to obtain additional data records. This is accomplished by varying one or more search parameters (e.g., age range, product code, keyword, etc.) In addition, functions are provided to extend the search/query capability beyond the predetermined parameters since virtually all successful computer based searches yield undesired as well as desired results. These functions address this problem by enabling the user to refine the search, primarily by implementing additional criteria to exclude irrelevant results.

These functions reconcile the wide variety of disparate words or phrases that may be used to describe similar incidents in the plurality of national or international databases queried by the invention. For example, "strangulation" may be indicated as "wrapped around neck". This variety of terms may further be subject to numerous spelling or grammatical erros (for example, "rapped arowned neck" instead of "wrapped around neck"). In light of these factors, users of the invention may wish to cast a "wide net" in their searches and use the above-mentioned functions to refine results in a semi-manual manner.

Continuing at step, 635, any presented records are screened or filtered to remove, reject or affirm presented records. This provides for searching in a hierarchical manner to locate desired data records. For example, if a query is submitted, at step 620, for "toy", typically this would result in a large number of records. However, by modifying the search criteria, from "toy" to "toy trucks", the search narrows the products found by the search. Alternatively, age ranges or year ranges may also be modified. In this repetitive manner, a hierarchical search may be accomplished to narrow, identify and/or reject records until the desired product and associated codes are located and affirmed.

If at step 625, the query is deemed sufficient, then at step 640, occurrence frequencies and severity levels of any found incidents associated with the query is established in accordance with the search parameters. At step 645, a prompt for report generation is provided. The reports may be selectively created in accordance with the data type, such as, for example, bar charts, graphs, charts, histograms, pie charts, tables, and/or or raw data records, or the like. The reports may use the pre-selected format type (e.g., standardized or native database format). At step 650, prompts may be presented for free-text input for executive summary and conclusion sections of the report. At step 655, actual data records may be optionally exported to be appended to the report. The process ends at step 660.

Figure 7:
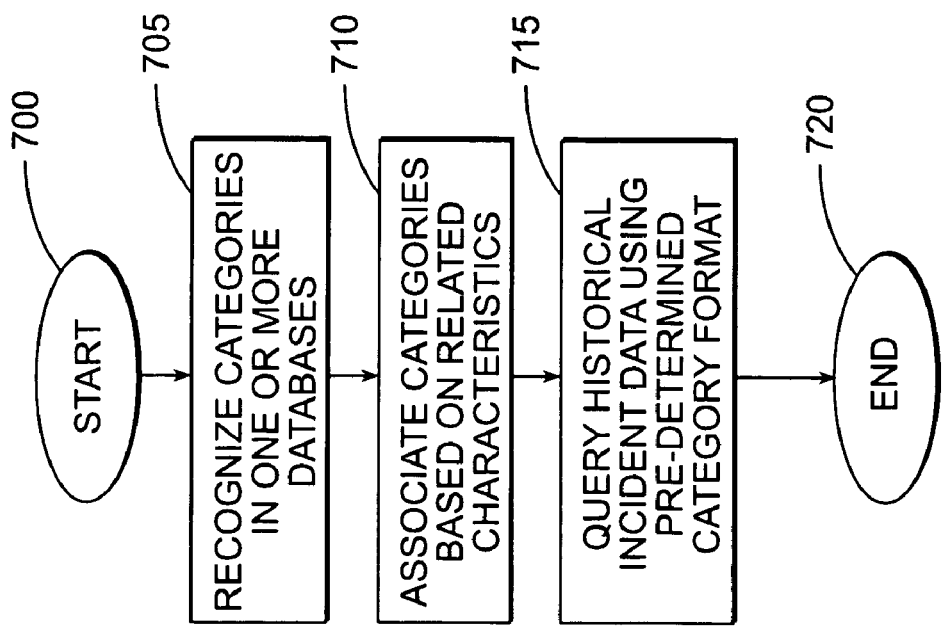
FIG. 7 is a flow diagram of an embodiment showing steps of implementing the invention.

FIG. 7 is a flow diagram an embodiment of steps of implementing the invention, starting at step 700. At step 705, one or more categories are recognized in one or more historical incident databases. At step 710, the categories are associated to a pre-defined format based on related or common characteristics which may be determined manually or by a confidence scoring process that recognizes common words, phrase or alphanumeric coding. The pre-defined format may be a standardized coding system that is unique or uses a coding format from an existing databases format. The pre-determined format provides a unifying coding to access the data across the databases when queried. At step 715, a query is made of the historical incident data using the pre-determined category format to obtain statistical information for outputting in a report, file or displays. The output provides a unified summary of the historical product in various formats once obtained by the query from the one or more databases and may reflect the standardized categories. The process ends at step 720.

Figure 8:
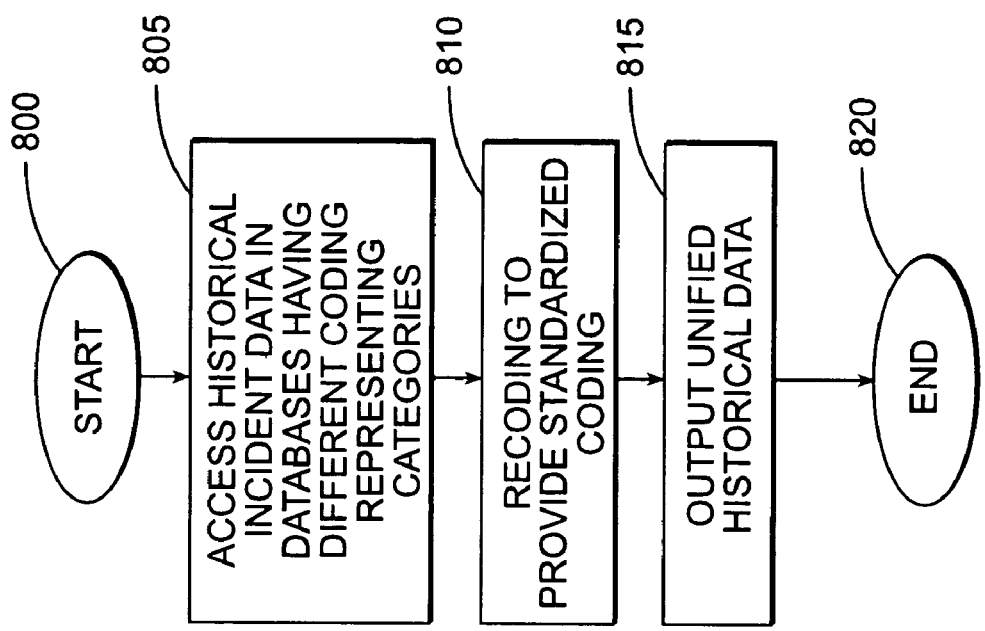
FIG. 8 is a flow chart of an embodiment showing steps of implementing the invention.

FIG. 8 is a flow chart of an embodiment showing steps of implementing the invention, starting at step 800. At step 805, historical incident data in one or more databases may be accessed by queries or search techniques typically using parameters from a user, or other sources such as a file. The data may have different coding that represents categories associated with the incident data. At step 810, the different coding is recoded to provide a standardized coding of the data in the one or more databases. At step 815, the historical incident data is outputted as unified data using the standardized coding representing standardized categories. The output may be reflected in various types of charts, graphs, and tables as appropriate. The output reflects the unified common coding of the source one or more databases. The process ends at step 820.

The invention provides for generation of severity scores and incident frequency indicators associated with a given set of query parameters and generates model cases that provide insight into typical modality and severity of injury. For example, the invention will generate one-to-many model cases in which mechanisms and/or severity of injury are linked to user-specified parameters such as age group, gender, location of incident, activity or behavior of victim, and product involved, where the number of model cases will be determined by user-specified or system-defined clustering criteria applied to the data.

The invention also provides for processing data through a plurality of techniques heretofore referred to as "mining" that include, but are not limited to statistical analysis, data mining, and/or artificial intelligence. In particular these techniques include knowledge extraction and document summarization methods used in the generation of model cases as one of ordinary skill in the art would recognize. These methodologies and techniques are described, for example, in McLachlan, G. J. 1992. *Discriminant Analysis and Statistical Pattern Recognition*, Wiley-Interscience; Fox, J. 1997. *Applied Regression Analysis, Linear Models, and Related Methods*, Sage Publications; Hosmer, D. W., and S. Lemeshow. 2000. *Applied Logistic Regression*, John Wiley & Sons; and Zhang, C. Q., and Zhang, S. C. 2002. *Association Rule Mining: Models and Algorithm*, Springer Verlag. Each of these publications is incorporated by reference herein. The mining techniques include, but are not limited to:

Clustering:
1. Hierarchical methods;
2. k-means; and
3. Discriminate analysis;

Principal component analysis;
Association rules;
Decision tress:
1. Classification trees; and
2. Regression trees;

Multiple linear regression (prediction);
Neural networks;
Support Vector Machines; and
Integration of supervised and unsupervised learning.

These methodologies are all well known in the art and a description herein is not required in order to understand the invention.

The invention and underlying plurality of databases may be used for various risk management objectives such as product risk reduction by manufacturers' introduction of new products, consumer buying awareness, professional research, government agencies, or the like. The invention further provides for extensive report generation that may present the data by standardized categories and sub-categories, any original contributing database format, cross-indexing among databases, ratings in any or all formats, characterization of any product by parameters (e.g. age, location, hazard type, severity, and/or frequency of occurrence). The reports may be presented in various forms such as graphics, tables, and/or text.

While the invention has been described in terms of embodiments, those skilled in the art will recognize that the invention can be practiced with modifications and in the spirit and scope of the appended claims.

What is claimed is:

1. A method of searching databases, comprising the steps of:
   accessing one or more databases each having historical incident data classified into categories;
   standardizing at least one of the categories of the historical incident data in the one or more databases by correlating incident data to a predetermined format;
   submitting a query for at least one of the standardized categories, wherein the query includes at least one of an age range parameter, a year range parameter, a keyword parameter and a product code parameter;
   checking whether a result of the query is sufficient, and if deemed sufficient, signifying an occurrence level and a severity level of incidents for records found during the query, otherwise, filtering the result of the query and resubmitting another query; and
   providing one or more outputs associated with the predetermined format for analysis.

2. The method of claim 1, further comprising the step of cross-referencing the categories among the one or more databases to find equivalent historical incident data for the correlating step.

3. The method of claim 1, wherein the accessing step comprises reading the one or more databases in a format native to each of the one or more databases.

4. The method of claim 1, wherein the categories for each of the one or more databases is database format dependent.

5. The method of claim 4, wherein at least one format of the one or more databases is different.

6. The method of claim 4, wherein at least one format of the one or more databases is one of partially different and wholly different.

7. The method of claim 1, wherein the standardizing step includes at least one of recoding numeric codes and text codes originally associated with the categories.

8. The method of claim 1, wherein the standardizing step generates standardized coding at least partially different from the coding of any of the one or more databases.

9. The method of claim 1, wherein the standardizing step generates standardized coding using a pre-existing coding of one of the one or more databases.

10. The method of claim 1, further comprising generating a report which synthesizes the one or more outputs.

11. The method of claim 10, wherein the generating step generates a report using one of a standardized coding and a native coding associated with one of the one or more databases.

12. The method of claim 1, further comprising submitting a query to search the historical incident data.

13. The method of claim 1, further comprising submitting a query to search standardized categories.

14. The method of claim 1, further comprising data mining and statistical mining the historical incident data.

15. The method of claim 1, further comprising data mining and statistical mining the standardized categories.

16. The method of claim 1, further comprising applying automated scoring to the historical incident data for generating severity scores and at-risk scores.

17. The method of claim 16, wherein at least one of severity scores and at-risk scores are associated with demographics.

18. The method of claim 16, wherein at least one of severity scores and at-risk scores are associated by at least one of product and product characteristic.

19. The method of claim 1, further comprising providing product information to be used as parameters for a search of the standardized categories.

20. The method of claim 1, further comprising providing product information to be used as parameters for a search of the one or more databases.

21. The method of claim 1, further comprising prompting for data sources.

22. The method of claim 1, wherein the historical incident data includes at least one of age data, injury data, fatality data, diagnosis data, injured body part data and disposition data.

23. The method of claim 1, wherein the providing step includes generating a report that includes accepting free-text input for inclusion in the report and exporting records from the one or more databases for inclusion in the report.

24. The method of claim 1, wherein the occurrence level includes a frequency indication of records found by the query and the severity level includes at least one of injury and fatality indication frequency.

25. A computer program product comprising a computer usable medium having readable program code embodied in the medium, the computer program product includes at least one component, when executed in a processor, to:
    access one or more databases each having historical incident data classified into categories;
    standardize at least one of the categories of the historical incident data in the one or more databases by correlating incident data to a predetermined format; and
    provide one or more outputs associated with the predetermined format for analysis,
    wherein the at least one component is configured to check whether a result of a query using the standardized at least one of the categories is sufficient, and if deemed sufficient, signifying an occurrence level and a severity level of incidents for records found during the query, otherwise, filtering the result of the query and resubmitting another query.

26. The computer program product of claim 25, wherein the occurrence level includes a frequency indication of records found by the query and the severity level includes at least one of injury and fatality indication frequency.

27. The computer program product of claim 25, wherein the at least one component cross-references the categories among the one or more databases to find equivalent historical incident data for the correlating step.

28. The computer program product of claim 25, wherein the at least one component reads the one or more databases in a format native to each of the one or more databases.

29. The computer program product of claim 25, wherein the categories for each of the one or more databases is database format dependent.

30. The computer program product of claim 25, wherein at least one format of the one or more databases is different.

31. The computer program product of claim 25, wherein at least one format of the one or more databases is one of partially different and wholly different.

32. The computer program product of claim 25, wherein the at least one component recodes at least one of numeric codes and text codes originally associated with the categories.

33. The computer program product of claim 25, wherein the at least one component generates standardized coding at least partially different from a coding of any of the one or more databases.

34. The computer program product of claim 25, wherein the at least one component generates standardized coding using a pre-existing coding of one of the one or more databases.

35. The computer program product of claim 25, wherein the at least one component generates a report which synthesizes the one or more outputs.

36. The computer program product of claim 25, wherein the at least one component generates a report using one of a standardized coding and a native coding associated with one of the one or more databases.

37. The computer program product of claim 25, wherein the at least one component submits a query to search historical product data.

38. The computer program product of claim 25, wherein the at least one component submits a query to search standardized categories.

39. The computer program product of claim 25, wherein the at least one component data mines and statistically analyzes the historical incident data.

40. The computer program product of claim 25, wherein the at least one component data mines and statistically analyzes the standardized categories.

41. The computer program product of claim 25, wherein the at least one component applies automated scoring to the historical incident data for generating severity scores and at-risk scores.

42. The computer program product of claim 41, wherein at least one of severity scores and at-risk scores are associated with demographics.

43. The computer program product of claim 41, wherein at least one of severity scores and at-risk scores are associated by at least one of product and product characteristic.

44. The computer program product of claim 25, wherein the at least one component provides product information to be used as parameters for a search of the standardized categories.

45. The computer program product of claim 25, wherein the at least one component provides product information to be used as parameters for a search of the one or more databases.

46. The computer program product of claim 25, wherein the at least one component prompts for data sources.

47. The computer program product of claim 25, wherein the at least one component submits a query, wherein the query includes at least one of an age range parameter, a year range parameter, a keyword parameter and a product code parameter.

48. The computer program product of claim 25, wherein the historical incident data includes at least one of age data, injury data, fatality data, diagnosis data, injured body part data and disposition data.

49. The computer program product of claim 25, wherein at least one component generates a report that includes accepting free-text input for inclusion in the report and exporting records from the one or more databases for inclusion in the report.

* * * * *